(12) United States Patent
Simon et al.

(10) Patent No.: US 10,499,961 B2
(45) Date of Patent: Dec. 10, 2019

(54) ENTRY PORTAL NAVIGATION

(75) Inventors: Bernd Simon, Kiel (DE); Arno Blau, Staufen im Breisgau (DE)

(73) Assignee: Stryker European Holdings I, LLC, Kalamazoo, MA (US)

(*) Notice: Subject to any disclaimer, the term of this patent is extended or adjusted under 35 U.S.C. 154(b) by 682 days.

(21) Appl. No.: 14/402,448

(22) PCT Filed: May 23, 2012

(86) PCT No.: PCT/EP2012/002206
§ 371 (c)(1),
(2), (4) Date: Apr. 8, 2015

(87) PCT Pub. No.: WO2013/174401
PCT Pub. Date: Nov. 28, 2013

(65) Prior Publication Data
US 2015/0216614 A1  Aug. 6, 2015

(51) Int. Cl.
*A61B 17/74* (2006.01)
*A61B 34/10* (2016.01)
(Continued)

(52) U.S. Cl.
CPC ............ *A61B 17/744* (2013.01); *A61B 34/10* (2016.02); *G16H 50/50* (2018.01);
(Continued)

(58) Field of Classification Search
CPC ....... A61B 19/50; A61B 34/10; A61B 17/744; A61B 2034/103; G06F 19/3437; A06B 2034/105; A06B 2034/107; A06B 2034/108; A61F 2002/30332; A61F 2002/30474; A61F 2002/30604;
(Continued)

(56) References Cited

U.S. PATENT DOCUMENTS 4,106,128 A * 8/1978 Greenwald ........... A61F 2/3804
623/21.13
4,524,766 A * 6/1985 Petersen ............... A61B 17/154
606/184

(Continued)

FOREIGN PATENT DOCUMENTS

EP        2363083 A1    9/2011
WO    2004069040 A2    8/2004
(Continued)

OTHER PUBLICATIONS

Image Registration Defined Archived on Apr. 2012 downloaded from https://en.wikipedia.org/w/index.php?title=Image_registration&oldid=488834006.*

(Continued)

*Primary Examiner* — Brian S Cook
(74) *Attorney, Agent, or Firm* — Lerner, David, Littenberg, Krumholz & Mentlik, LLP

(57) ABSTRACT

A method and a corresponding device is proposed, for determining a location on a bone surface and for performing a simulation of an insertion of an implant based on the determined location. The simulation may comprise the steps of identifying an implantation axis of the bone in the first image, and aligning a visualization of the implant with the implantation axis, with respect to the determined location.

22 Claims, 8 Drawing Sheets

(51) Int. Cl.
*G16H 50/50* (2018.01)
*A61B 17/17* (2006.01)
(52) U.S. Cl.
CPC ..... *A61B 17/1725* (2013.01); *A61B 2034/102* (2016.02); *A61B 2034/105* (2016.02); *A61B 2034/107* (2016.02); *A61B 2034/108* (2016.02)
(58) Field of Classification Search
CPC .. A61F 2002/30617; A61F 2002/30784; A61F 2002/30787; A61F 2002/30794; A61F 2002/30827; A61F 2002/30968; A61F 2002/3625; A61F 2002/3639
USPC .......................................................... 703/6
See application file for complete search history.

(56) References Cited

U.S. PATENT DOCUMENTS

| | | |
|---|---|---|
| 5,398,684 A | 3/1995 | Hardy |
| 5,799,055 A | 8/1998 | Peshkin et al. |
| 6,064,932 A | 5/2000 | Fran.cedilla.ois |
| 6,198,794 B1 | 3/2001 | Peshkin et al. |
| 6,470,207 B1* | 10/2002 | Simon ............... A61B 34/20 378/207 |
| 6,682,565 B1* | 1/2004 | Krishnan ............ A61F 2/4241 623/21.16 |
| 6,701,174 B1 | 3/2004 | Krause et al. |
| 6,711,432 B1 | 3/2004 | Krause et al. |
| 9,119,722 B1* | 9/2015 | Kusuma ............... A61F 2/36 |
| 2004/0068187 A1* | 4/2004 | Krause ............... A61B 17/15 600/443 |
| 2004/0111024 A1 | 6/2004 | Zheng et al. |
| 2004/0240715 A1 | 12/2004 | Wicker et al. |
| 2005/0251113 A1 | 11/2005 | Kienzle, III |
| 2006/0015188 A1* | 1/2006 | Grimes ........... A61B 17/1668 623/23.19 |
| 2007/0270680 A1* | 11/2007 | Sheffer ............... A61B 90/36 600/407 |
| 2008/0075348 A1 | 3/2008 | Rappaport et al. |
| 2008/0175464 A1 | 7/2008 | Brett et al. |
| 2008/0294265 A1* | 11/2008 | Warkentine ....... A61B 17/1746 623/22.4 |
| 2008/0319448 A1* | 12/2008 | Lavallee ............. G06F 17/50 606/102 |
| 2009/0017430 A1* | 1/2009 | Muller-Daniels ...... G09B 23/30 434/262 |
| 2009/0209851 A1* | 8/2009 | Blau ................ A61B 17/1703 600/426 |
| 2010/0241129 A1 | 9/2010 | Markey et al. |
| 2011/0082367 A1 | 4/2011 | Regazzoni |
| 2011/0092804 A1* | 4/2011 | Schoenefeld ........ A61B 17/151 600/416 |
| 2011/0213379 A1 | 9/2011 | Blau et al. |
| 2012/0106819 A1 | 5/2012 | Fernandez Oca |
| 2013/0211386 A1 | 8/2013 | Blau et al. |
| 2013/0317512 A1 | 11/2013 | Buhren et al. |
| 2015/0164445 A1 | 6/2015 | Blau et al. |
| 2015/0265361 A1 | 9/2015 | Blau et al. |
| 2016/0278824 A1 | 9/2016 | Toy |
| 2016/0296285 A1 | 10/2016 | Chaoui et al. |
| 2016/0354156 A1 | 12/2016 | Blau et al. |

FOREIGN PATENT DOCUMENTS

| | | |
|---|---|---|
| WO | 2010121147 A1 | 10/2010 |
| WO | 2010122145 A1 | 10/2010 |

OTHER PUBLICATIONS

Extended European Search Report for Application No. EP12169104 dated Sep. 3, 2012.
Dahlen et al. "Computer-assistierte OP-Planung", Der Unfallchirurg, vol. 104, No. 6, Jun. 1, 2001 (Jun. 1, 2001), pp. 466-479, XP55036111.
Zheng et al, "Reality-augmented virtual fluoroscopy for computer-assisted diaphyseal long bone fracture osteosynthesis: a novel technique and feasibility study results", Proceedings of the Institution of Mechanical Engineers.Journal of Engineering in Medicine. Part H, Mechanical Engineering Publications LTD, London, GB, vol. 222, No. H1, Jan. 1, 2008 (Jan. 1, 2008), pp. 101-115, XP009162175.
Guoyan Zheng et al, "A hybrid CT-free navigation system for total hip arthroplasty", Computer Aided Surgery, vol. 7, No. 3, Jan. 1, 2002 (Jan. 1, 2002), pp. 129-145, XP55036140.
Schulz et al., "Evidence Based Development of a Novel Lateral Fibula Plate (VariAx Fibula) Using a Real CT Bone Data Based Optimization Process During Device Development", The Open Orthopaedics Journal, 2012, 6, 1-7.
International Search Report for Application No. PCT/EP2012/002207 dated Feb. 8, 2013.
International Search Report for Application No. PCT/EP2012/002206 dated Feb. 12, 2013.

* cited by examiner

ENTRY PORTAL NAVIGATION

CROSS-REFERENCE TO RELATED APPLICATIONS

The present application is a national phase entry under 35 U.S.C. § 371 of International Application No. PCT/EP2012/002206 filed May 23, 2012, published in English as WO 2013/174401 A1, which is hereby incorporated herein by reference.

FIELD OF THE INVENTION

The invention relates to the field of computer assisted surgery. Particularly, the invention relates to a computer software based method for identifying an entry point at a bone for assisting an insertion of an implant. Furthermore, the invention relates to a corresponding device.

BACKGROUND OF THE INVENTION

Usually, an implant is inserted into a bone based on the experience of a physician. In other words, the physician opens the tissue surrounding the bone, tries to identify a known landmark on the bone surface, and introduces an implant through a chosen point on the bone surface. In particular in a case in which a bone nail should be inserted into a tubular bone, there is a significant risk of displacement of the bone nail so that the bone nail itself or a locking screw being introduced through a transverse bore in the bone nail, is finally positioned within the bone with the positioning being far from optimal.

US 2011/0213379 A1 discloses a computer assisted surgery system and a method for operating the same, wherein the method includes providing a visualization of a virtual representation of a medical device in the anatomical context to facilitate an application of the medical device.

SUMMARY OF THE INVENTION

It is an object of the invention to provide means for identifying a suitable entry point at a bone for assisting an insertion of an implant and for achieving better implantation results. It is a further object to reduce an amount of radiation to which a patient is exposed during an insertion of an implant. These and other objects are achieved by the subject-matter of each of the independent claims. Further embodiments are described in the respective dependent claims.

According to a first aspect, a method comprises, in general, the steps of determining a location on a bone surface in a first image generated from a first direction, and performing a simulation of an insertion of an implant based on the determined location. The simulation comprises the steps of identifying an implantation axis in the first image, and aligning a visualization of the implant with the implantation axis, with respect to the determined location.

Depending on the intended application, the implantation axis may be orientated substantially parallel to a longitudinal shaft axis of a long bone or in a transverse direction to the shaft axis. For example, if the implant is a bone nail adapted for an implantation within the medullary channel of a tubular bone, the implantation axis is substantially the longitudinal shaft axis of the bone. On the other hand, if the implant is a bone screw adapted for fixing parts of a fractured bone, the implantation axis may have any orientation, i.e. may be at least partially transverse or inclined to the longitudinal axis of the bone. Furthermore, if the implant is a locking screw adapted to be inserted through a bore in a bone plate or bone nail, the implantation axis is substantially identical to the bore axis.

The data of the first image may be received directly from an imaging device, for example from a 2D C-arm based X-ray device. The image may represent an anatomical structure of interest, in particular a bone. The image may otherwise be received from a database at which previously recorded images are stored. Furthermore, the image may be a 2D visualization of a 3D computer tomography, a 3D ultrasound or a rotational X-ray scan. Based on already existing images, the described method and system may be used for training purposes.

According to an embodiment, at least the simulation is performed by a computer program comprising corresponding sets of instructions.

It will be understood that the method step of determining a location on a bone surface may be performed manually by means of a suitable pointing device, wherein a suitable pointing device may be a cursor of a computer mouse. Otherwise, the method step of determining a location on a bone surface may be performed automatically, for example by means of a reference object visible in the image, wherein the reference object may be for example a tip of an instrument or an element like an arrow laying under the patient during the imaging.

It will be understood that the computer program may therefore further include sets of instructions to identify a bone surface and the reference object in the image.

A corresponding computer program may preferably be loaded into a work memory of a data processor. The data processor or processing unit may thus be equipped to carry out at least a part of the method described herein. Further, the invention relates to a computer-readable medium such as a CD-ROM at which the computer program may be stored. However, the computer program may also be presented over a network like the World Wide Web and can be downloaded into the working memory of the data processor from such a network.

According to another embodiment, the simulation may further comprise the step of introducing a visualization of a sub-implant which may be implanted in combination with the implant, with respect to a positioning of the implant. Therefore, the positioning of the sub-implant is based on the positioning of the implant and is thus based indirectly on the determined location which represents the entry point of the implant.

It is noted that the positioning of the implant includes both a translational and a rotational orientation of the implant relative to for example a bone.

According to another embodiment, the method further comprises the steps of determining a deviation of the positioning of the implant and/or of the sub-implant according to the simulated insertion from an optimal positioning. A further step may be, if the deviation is within a predetermined range, identifying the determined location as suitable entry point for an insertion.

According to a further embodiment, the determination of a location on a bone surface is performed utilizing a bone model. For example, a 3D model of a bone which corresponds to the bone imaged in the first image may be received from a database. An exemplary utilization of bone models is described in 'Evidence based development of a novel lateral fibula plate (VariAX Fibula) using a real CT bone data based optimization process during device development' of A. P. Schulz et al. (The Open Orthopaedics Journal, 2012, 6, 1-7), the content of which is incorporated herein by reference.

According to another embodiment, the method may additionally be performed on the basis of a second image generated from a second direction, wherein the second direction may be substantially perpendicular to the first direction.

By way of these embodiments (alone or combination), an entry point may be identified more accurately on the three dimensional surface of a bone model or an imaged bone.

According to yet another embodiment, the optimal positioning includes a depth and a rotation of the implant relative to the bone. The optimal positioning may further include a length of a sub-implant.

As mentioned above, a criterion for an entry point may be a deviation of the virtual positioning of the implant from an optimal positioning. The optimal positioning may depend on at least one of the aspects from the group consisting of: the implant is located within the bone, the axis of the implant is aligned to the axis of the bone, the implant is located within a medullary cannel of a tubular bone, and the implant is not significantly bended (indicating that only small forces act in a transverse direction).

For example, assuming that an optimal positioning of a bone nail (an implant) is such that the axes of the bone nail and a tubular bone like a femur are identical, i.e. congruent, and further assuming that the bone nail is implanted into a medullary channel of the femur so that the longitudinal axis of the bone nail is not congruent but substantially parallel to the longitudinal axis of the femur, i.e. the bone nail is located within the medullary channel but is slightly shifted to a side, then the actual positioning of the bone nail has a deviation from the optimal positioning which may be determined as small and to be tolerated. However, if the axis is shifted such that a sub-implant like a locking screw if inserted, would be positioned in an inappropriate manner, for example an end or a portion of the sub-implant would be not completely within the bone or with a distance from the outer surface of the bone which may be determined as too small, then the actual positioning of the bone nail together with a sub-implant have a deviation from the optimal positioning which may be determined as too large, i.e. should not be tolerated.

A deviation as well as a corresponding predetermined range may be defined by percent, in a case in which the optimal positioning is determined by a length or a diameter, or may be defined by a distance, in a case in which the optimal positioning is determined by a position or axis.

It is noted that the steps of the method may be repeated to iteratively achieve a more accurate identification of an entry point.

According to a further embodiment, the step of determining a location on a bone surface does not include a positioning of a pointing device at a bone surface in so far as the step constitutes a treatment of a human or animal body by surgery.

According to a further aspect, a device for identifying an entry point on a bone surface of a bone for assisting an insertion of an implant, comprises, in general, a processing unit adapted for determining a location on the bone surface which is a possible entry point, based on an image of the bone including the bone surface, and performing a simulation of an insertion of an implant into the bone with respect to the determined location.

It will be understood that a virtual implant having a suitable size and shape may be selected out of a group of virtual implants with differing sizes and shapes. Accordingly, the device may further comprise a database for storing a plurality of visualizations of virtual implants. The processing unit may in this case further be adapted for automatically selecting an implant out of the group of implants.

On the other hand, the size and shape of one virtual implant may be adapted as needed. Therefore, the processing unit of the device may further be adapted for adapting the virtual visualization of the implant to the imaged bone that is the size and/or shape of the virtual visualization to the imaged bone.

It is noted that also the size and/or shape of an implant selected out of a group of implants may be adapted to an imaged bone if necessary.

Furthermore, the processing unit may be adapted for registering the virtual visualization of the implant with the received image.

The device may further comprise an imaging unit for generating images of the bone from different directions. The imaging unit may be an X-ray imaging device for generating X-ray images.

According to a further embodiment, the system further comprises input means for manually determining a location on a bone surface. Such input means may be for example a computer keyboard, a computer mouse or a touch screen, to control a pointing device like a cursor on a monitor screen.

According to yet another embodiment, the device further comprises a pointing device visible in the received image. If the image is received from an X-ray imaging device, the pointing device may include a radiolucent shaft and a radiopaque tip adapted to represent a reference object visible in an X-ray image and adapted to point to a location on a bone surface. The tip may be in contact with the location on the bone surface. Additionally, the pointing device may comprise at least one radiopaque element arranged at a predetermined position relative to the tip so that the position of the tip may be clearly identified in an X-ray image.

It is noted, that the processing means may be realized by only one processor performing all the steps, or by a group or plurality of processors, for example a system processor for processing the image data including an identification of anatomical structures like a bone surface, a separate processor specialized on a simulation of a implantation of an implant, and a further processor for controlling a monitor for visualizing the result.

Furthermore, the system may comprise storage means providing a database of implants and/or bone models. It will be understood, that such storage means may also be provided in a network to which the system may be connected and information related to the implant, i.e. different types of implants and parameter thereof, may be received over that network.

It has to be noted that embodiments are described with reference to different subject-matters. In particular, some embodiments are described with reference to method type claims (computer program) whereas other embodiments are described with reference to apparatus type claims (system). However, a person skilled in the art will gather from the above and the following description that unless other notified in addition to any combination of features belonging to one type of subject-matter also any combination between features relating to different subject-matters is considered to be disclosed with this application.

The aspects defined above and further aspects, features and advantages of the described methods and devices can also be derived from the examples of the embodiments to be described hereinafter and are explained with reference to

Figure 1:
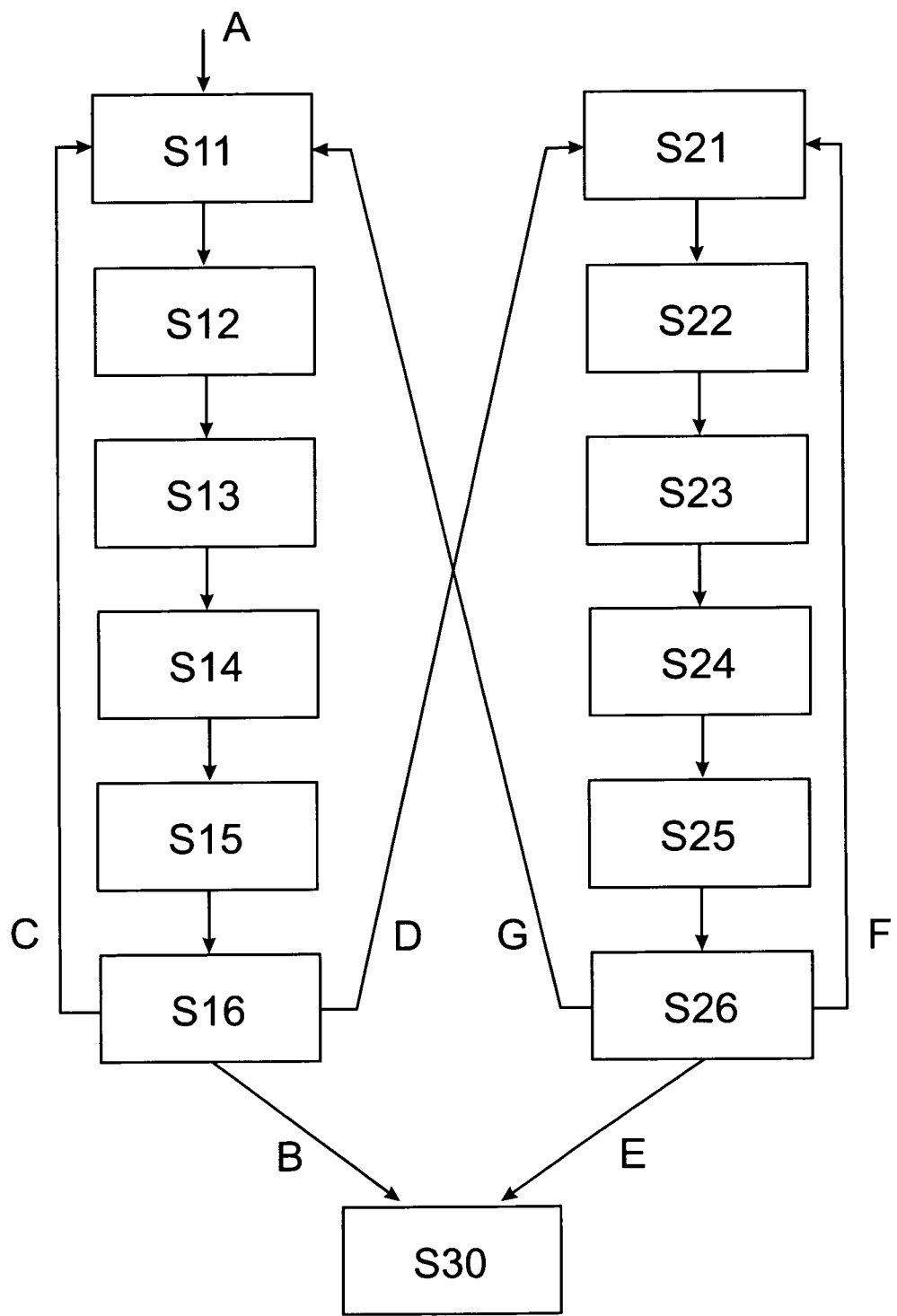
FIG. 1 shows a flow chart of steps performed in accordance with an embodiment described herein.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION OF THE EMBODIMENTS

The flow-chart in FIG. 1 illustrates the principle of the steps performed in accordance with an embodiment described herein. It will be understood that the steps described, are major steps, wherein these major steps might be differentiated or divided into several sub-steps. Furthermore, there might be also sub-steps between these major steps.

Several possibilities of performing a method are provided in accordance with FIG. 1.

Starting at arrow A, an image is received for example from an X-ray imaging unit in step S11, the image being generated from a first direction. In step S12, a location on a bone surface is determined.

In steps S13, S14, a simulation of an implantation of an implant is performed, based on the location on the bone surface determined in step S11. In other words, an implantation is simulated starting from the previously determined location. As a result, the virtual implant is positioned within the imaged bone, as if it would have been introduced with the determined location as an entry point. The result may be shown on a display or monitor, for example as an overlay of the virtual implant on the image received in step S11.

In step S13, a shaft axis of for example a tubular bone is identified. In step S14, an axis of the virtual implant is aligned with the identified implantation axis. Optionally, a sub-implant like a locking screw is introduced in step S15.

In step S16, a deviation of the positioning of the virtual implant from an optimal positioning is determined. This may be performed by comparing the positioning of the virtually implanted implant with another implant which is also visualized as an overlay on the image on a theoretically optimal position.

Following arrow B as a first alternative, in case in which the deviation is within a predetermined range, the initially determined location is identified as suitable entry point in step S30.

Following arrow C as a second alternative, in case in which the deviation is not within a predetermined range, the steps S11 to S16 are performed again, wherein a new image with a new location is now received in step S11. By repeating this part of the method, a result can be iteratively achieved, having a deviation within a predetermined range.

Following arrow D as a third alternative, method steps S21 to S26 are performed, wherein these steps are similar to steps S11 to S16. The image received in step S21 is alternatively generated based on image data received from an imaging device or based on bone model data received from a database. The anatomical structures are shown in the resulting visualization from a second direction differing from the first direction in step S11.

When step S22 is performed the first time, i.e. following arrow D to step S21, the location determined in step S12 is used as a starting point for the simulation performed in steps S23 to S25.

As in step S16, three alternatives exist following step S26.

Following arrow E as a first alternative, in case in which a deviation of the positioning of the virtual implant from an optimal positioning based on an image generated from a second direction, as determined in step S26, is within a predetermined range, the location determined in step S22 is identified as suitable 3D entry point in step S30. It is noted that the location identified as suitable entry point in step S16 based on an image generated from a first direction, may be identified as suitable also in step S26 based on an image generated from a second direction.

Following arrow F as a second alternative, in case in which a deviation is not within a predetermined range, the part of the method including steps S21 to S26 is repeated, to iteratively determine a location based on an image generated from a second direction, which location leads to a positioning as a result of a simulated implantation with a deviation from an optimal positioning within a predetermined range.

It is noted that on the basis of only one X-ray image together with information taken from a bone model, an accurate determination of a three dimensional entry point may be provided in accordance with the alternatives following arrows E and/or F.

Following arrow G as a third alternative, the first part of the method, i.e. steps S11 to S16 are repeated. This path may be performed in a case in which the location identified as suitable by steps S21 to S26 differs clearly from that identified as suitable by previously performed steps S11 to S16.

Following arrows D and G several times lead to a method of iteratively determining a three dimensional location on a bone surface as an entry point finally identified in step S30 as suitable for an insertion of an implant into the bone.

Figure 2:
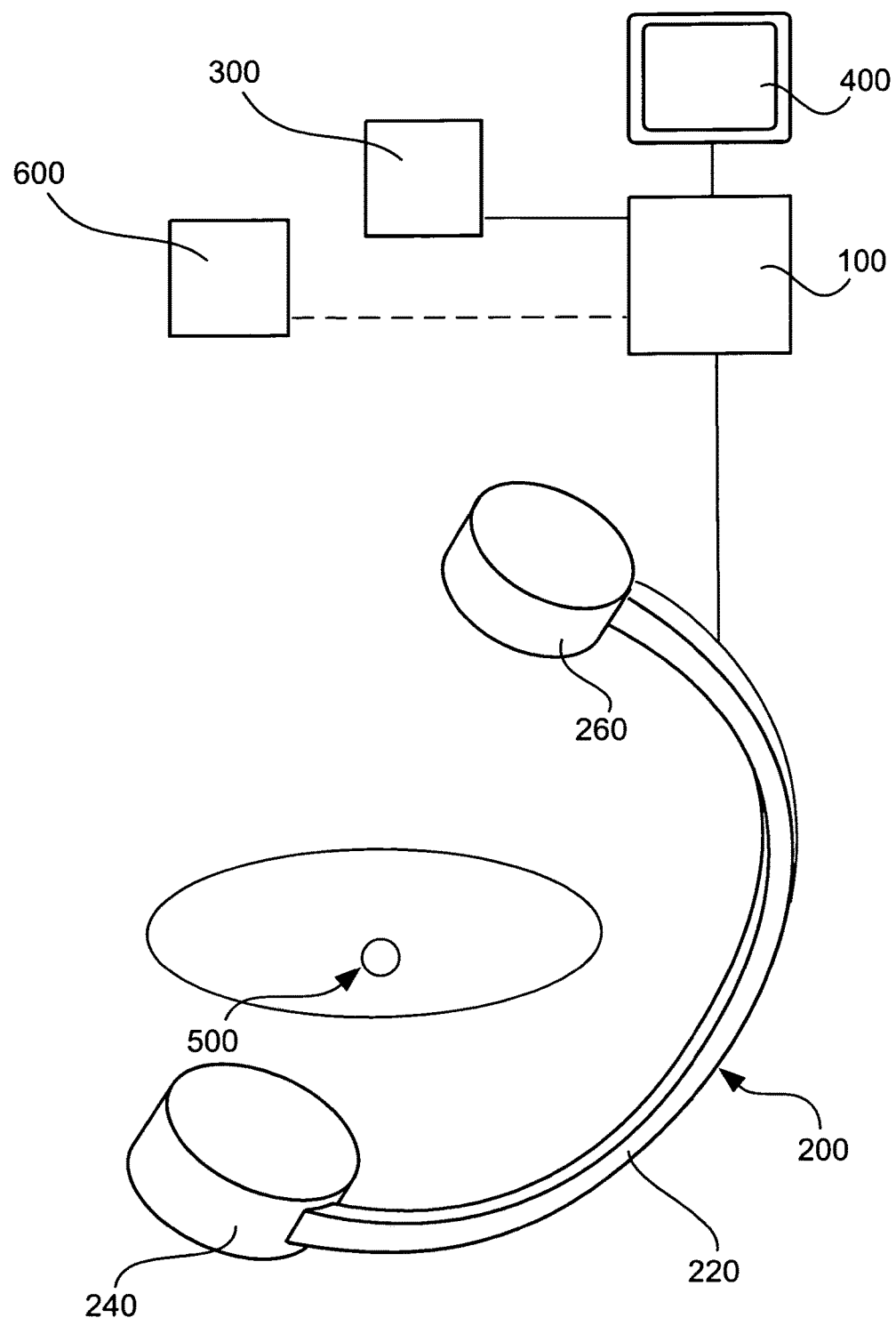
FIG. 2 shows a schematical illustration of a system according to an embodiment described herein.

FIG. 2 shows an exemplary embodiment of a device. Substantially necessary for performing the steps described herein, the device comprises a processing unit 100 and a monitor 400.

The exemplary imaging device 200 includes an X-ray source 240, and an X-ray detector 260, wherein these two devices are mounted on a C-arm 220. It will be understood that the device may also comprise another non-invasive imaging modality like a computer tomography device, a magnetic resonance device, or an ultrasound device as imaging device instead of or additional to the shown C-arm based X-ray device.

Furthermore, the device in FIG. 2 includes an input device 300, by means of which for example a manual determination of a location on a bone surface may be performed. Also shown is a connection (as dotted line) to a database 600, located for example in a network.

Finally, there is shown a region of interest 500. Within said region, for example a bone of a patient may be located, wherein it is intended to introduce an implant into that bone, but a suitable entry point for the implantation has to be identified.

In FIGS. 3 to 8, exemplary visualizations are shown. Each of these visualizations represents for example an X-ray image of a hip joint with a femur 10, including the contour of the hip bone and the femur. Additionally, a pointing device, an implant and/or a sub-implant is shown.

Figure 3:
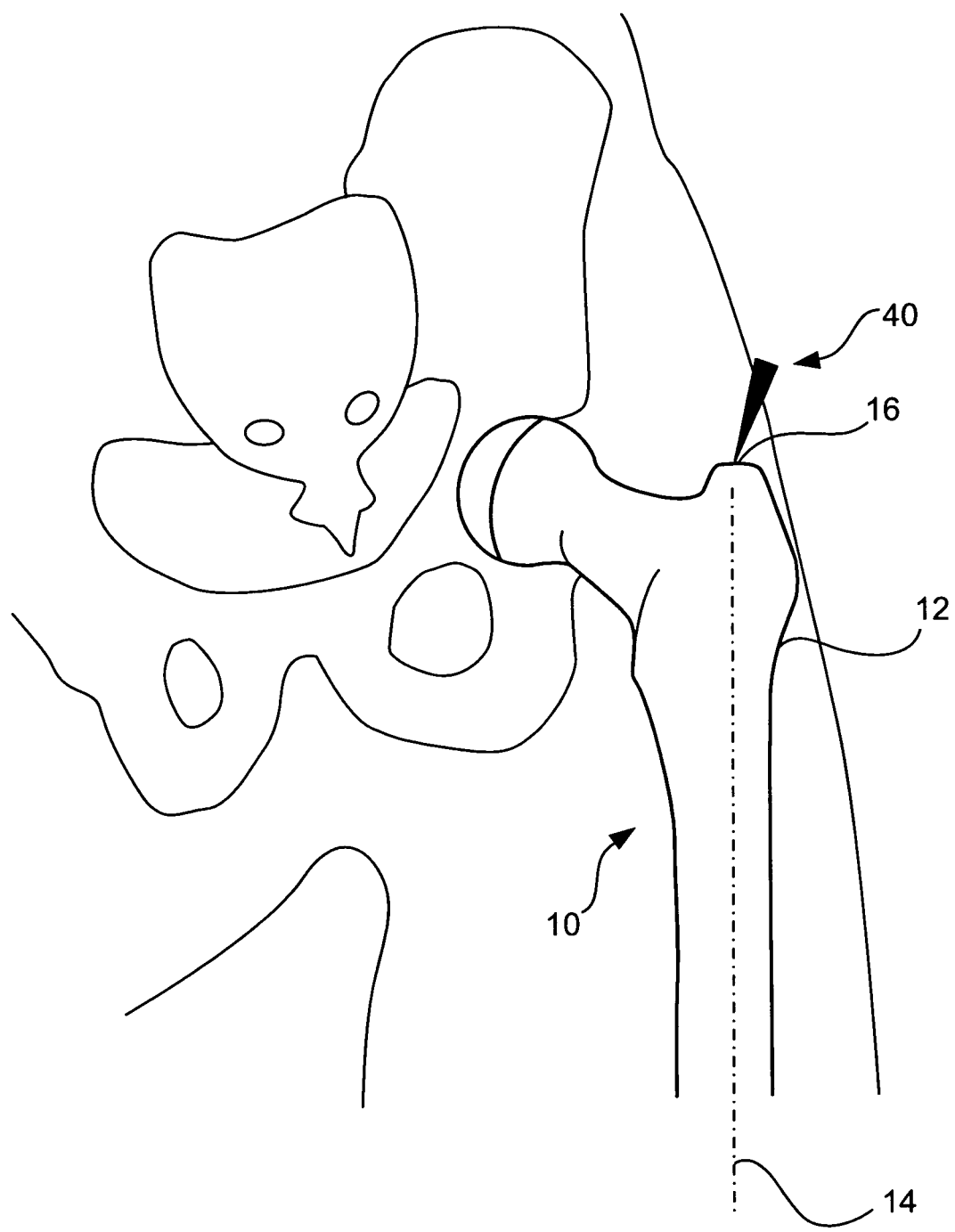
FIG. 3 shows an exemplary image generated from a first direction including anatomical structures and a pointing device.

FIG. 3 shows a situation in which the method steps S11 and S12 are performed, i.e. an image is received and a location is determined on the bone surface.

In FIG. 3, the hip bone and femur are shown from an anterior-posterior direction as a first direction. The femur 10 comprises a bone surface 12 and a longitudinal axis 14. By means of the pointing device 40, a location 16 is determined on the bone surface. The pointing device 40 in FIG. 3 may be for example a cursor of a computer mouse.

Figure 4:
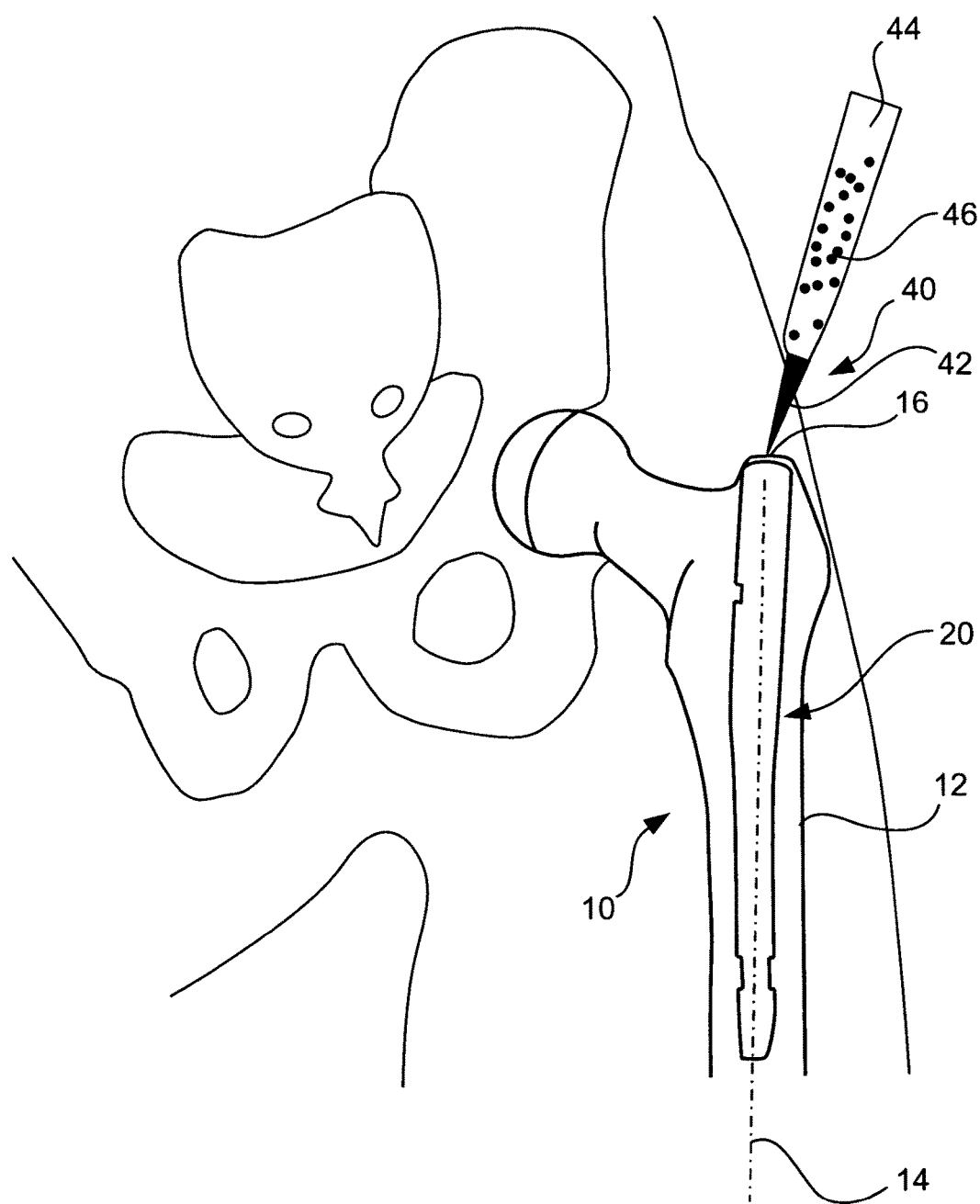
FIG. 4 shows an exemplary image including anatomical structures, a pointing device and a virtual visualization of an implant.

FIG. 4 shows a situation in which the steps S11 to S14 are performed, i.e. an implant is virtually implanted based on the previously determined location on the bone surface.

In FIG. 4, a pointing device 40 is shown, having a tip 42, a shaft 44 and elements 46, wherein the tip 42 and the elements 46 may be radiopaque to be visible in an X-ray image, and the shaft 44 may be radiolucent to be not visible in the X-ray image. Since the X-ray image is a 2D projection of a 3D object, the pointing device may be located in any depth. The tip 42 of the pointing device 40 may be in contact with the bone surface 12 at the location 16 so that the contact point can be determined as the location in the X-ray image.

As an overlay, a visualization of an implant 20, i.e. a bone nail, is additionally shown in FIG. 4, wherein the implant 20 is aligned with the longitudinal shaft axis 14 of the femur 10.

Figure 5:
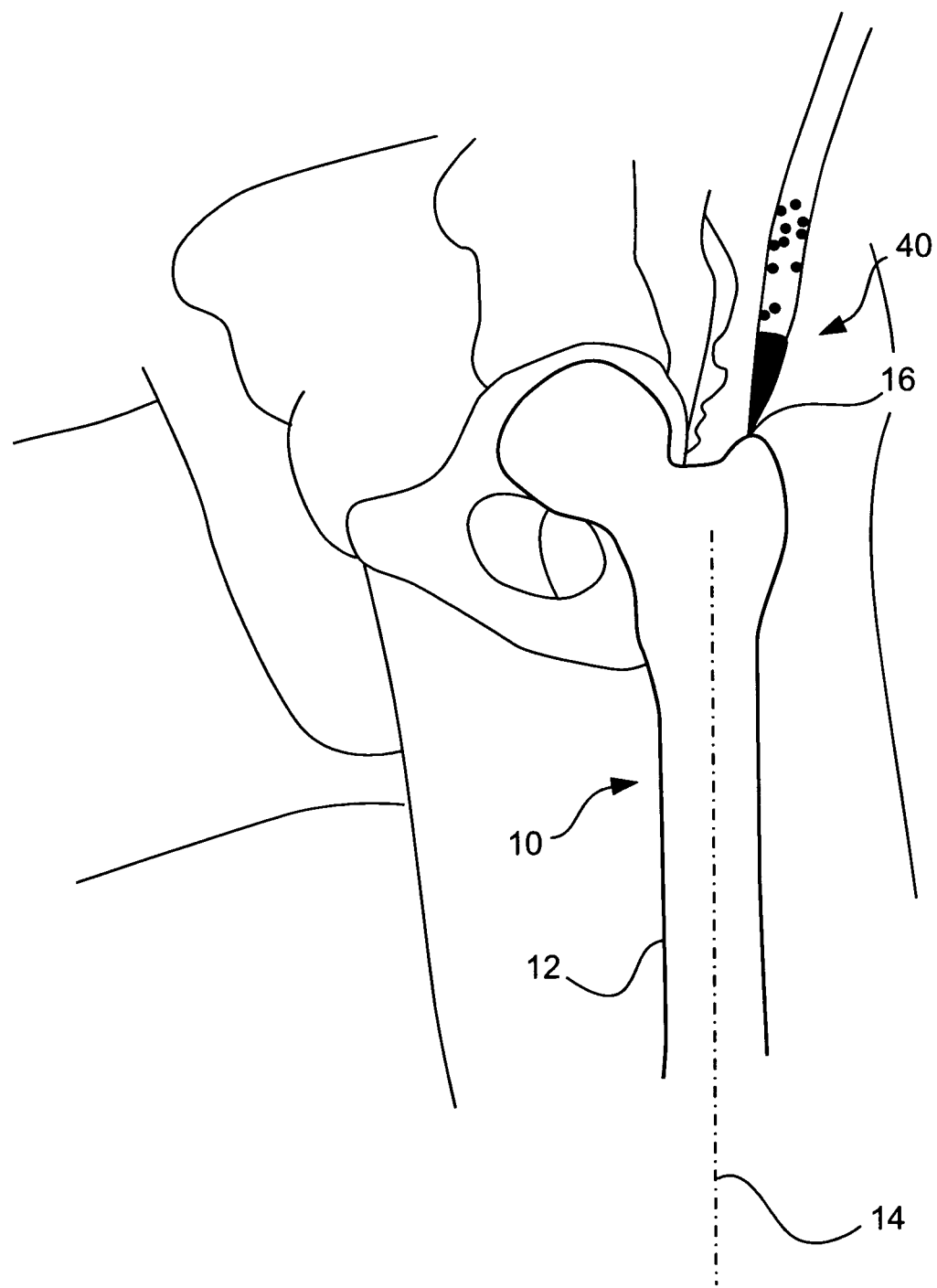
FIG. 5 shows an exemplary image including anatomical structures and a pointing device shown from a second direction.

FIG. 5 shows the situation in which steps S21 and S22 are performed, i.e. an image visualizing a femur from a second direction is generated based on a bone model from a database or is received from an imaging device and a location is determined. It is noted that the femur may be also visualized without the surrounding anatomical structures, in particular in a case in which the image is generated based on a bone model.

In FIG. 5, the femur 10 includes a bone surface 12 and a shaft axis 14. The pointing device 40 is visible with its tip at the location 16 on the bone surface.

Figure 6:
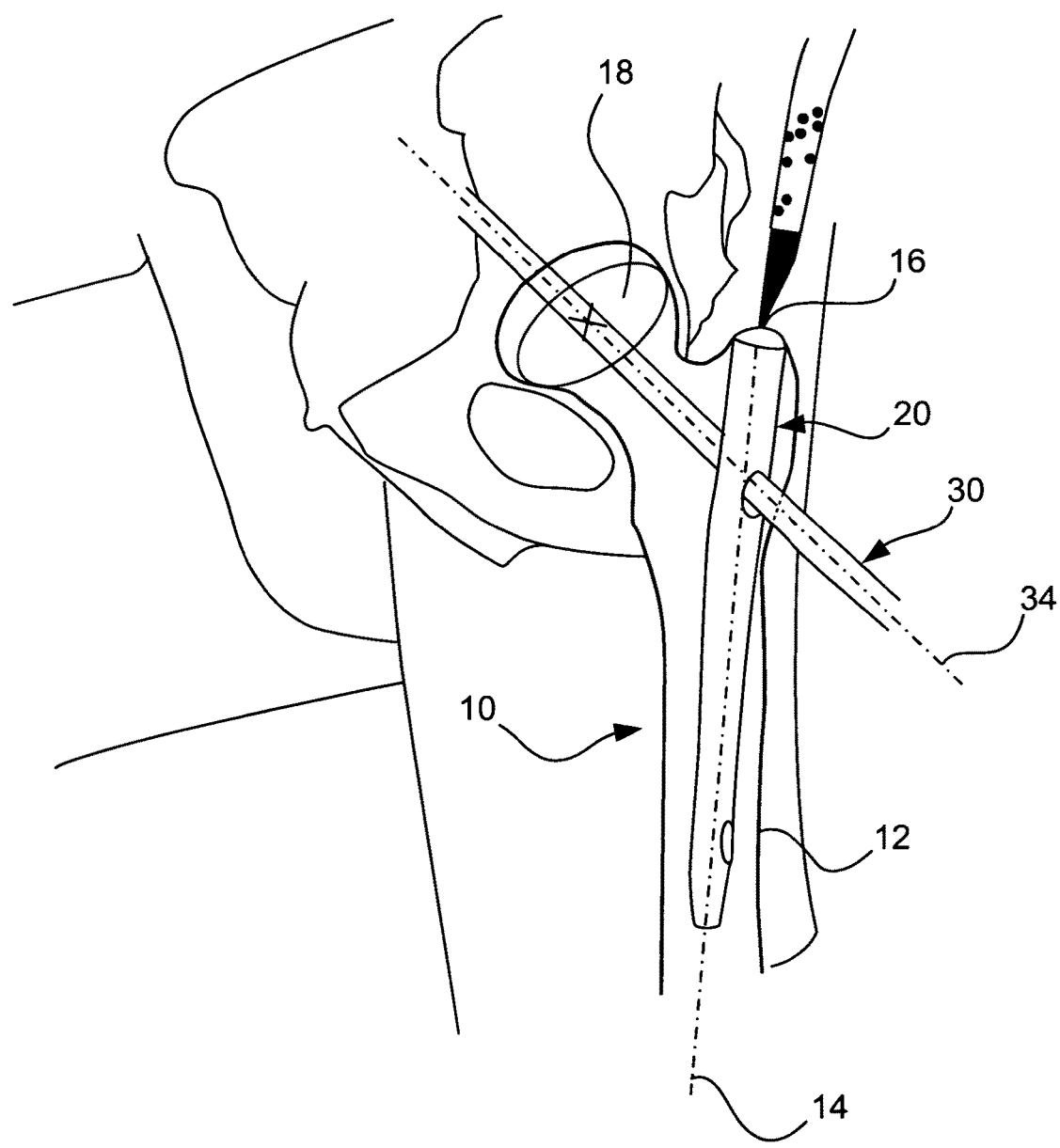
FIG. 6 shows an exemplary image including anatomical structures, a pointing device and a virtual visualization of an implant and a sub-implant axis.

FIG. 6 shows a situation in which steps S21 to S25 are performed, i.e. not only an implant is virtually implanted but also a sub-implant.

In FIG. 6, a hip joint with a hip bone and a femur 10 is shown, wherein the hip joint is imaged from a medial-lateral direction as the second direction which is substantially perpendicular to the first direction of FIGS. 3 and 4. The femur 10 comprises a bone surface 12 and a longitudinal shaft axis 14. By means of the pointing device 40, the location 16 is determined. Furthermore, the femur head 18 is identified by a center point and a diameter. Further shown in FIG. 6 is an implant 20 together with a sub-implant 30, both substantially including a longitudinal axis and a diameter, wherein the axis of the implant 20 is aligned with the axis 14 of the femur and the axis 34 of the sub-implant extends through the center point of the femur head 18.

Figure 7:
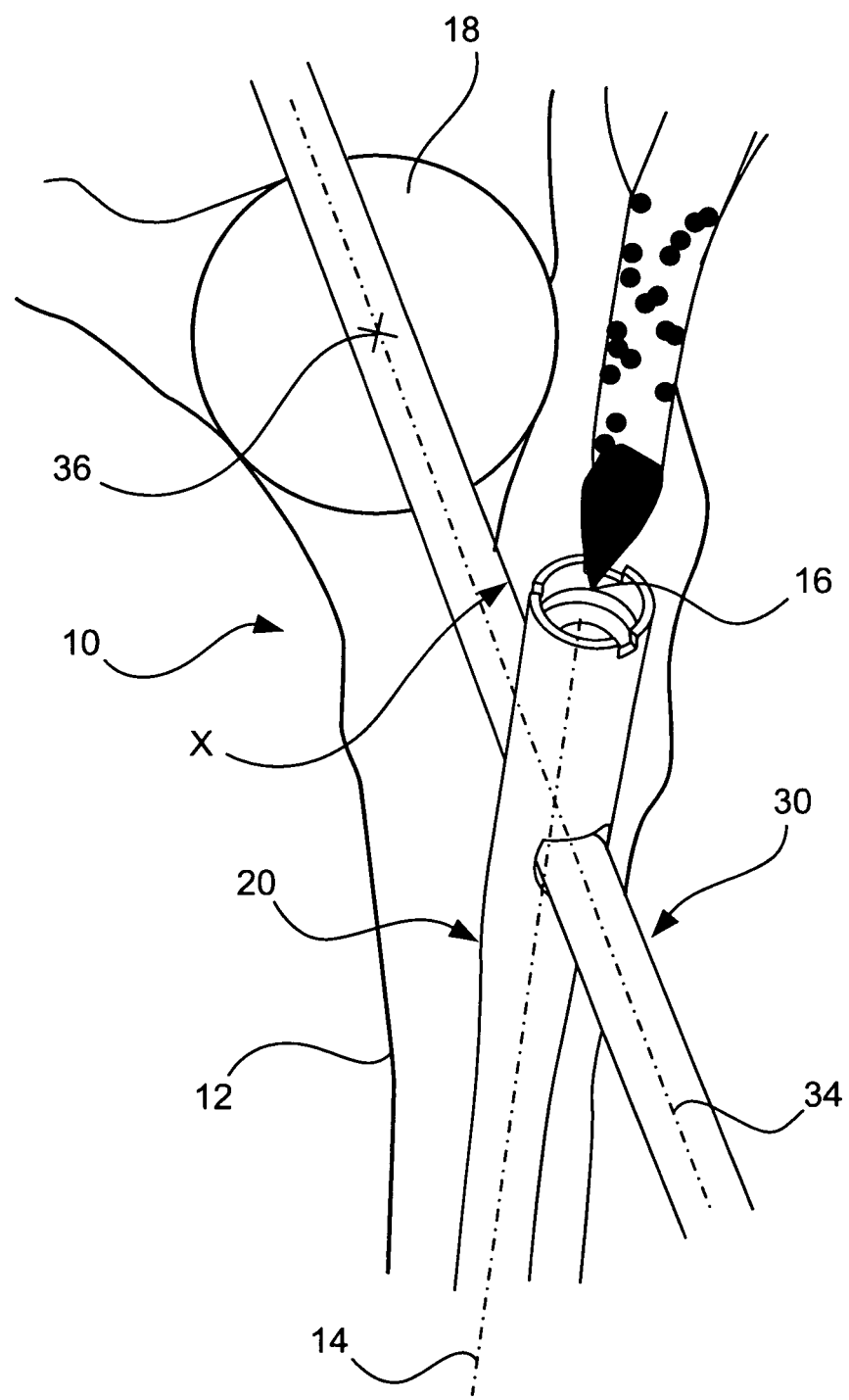
FIG. 7 shows an exemplary isometrical image including anatomical structures, a pointing device and a virtual visualization of an implant and a sub-implant axis.

FIG. 7 shows a situation as in FIG. 6, i.e. in which steps S21 to S25 are performed. The situation in FIG. 7 differs from that in FIG. 6 in that the virtually implanted sub-implant 30 significantly deviates from an optimal positioning. Indicated by the reference sign X is an area of the femur neck at which the sub-implant would protrude out of the bone. Accordingly, the location 16 in FIG. 7 is inappropriate as an entry point for an implantation of the implant 20 and the sub-implant 30.

Figure 8:
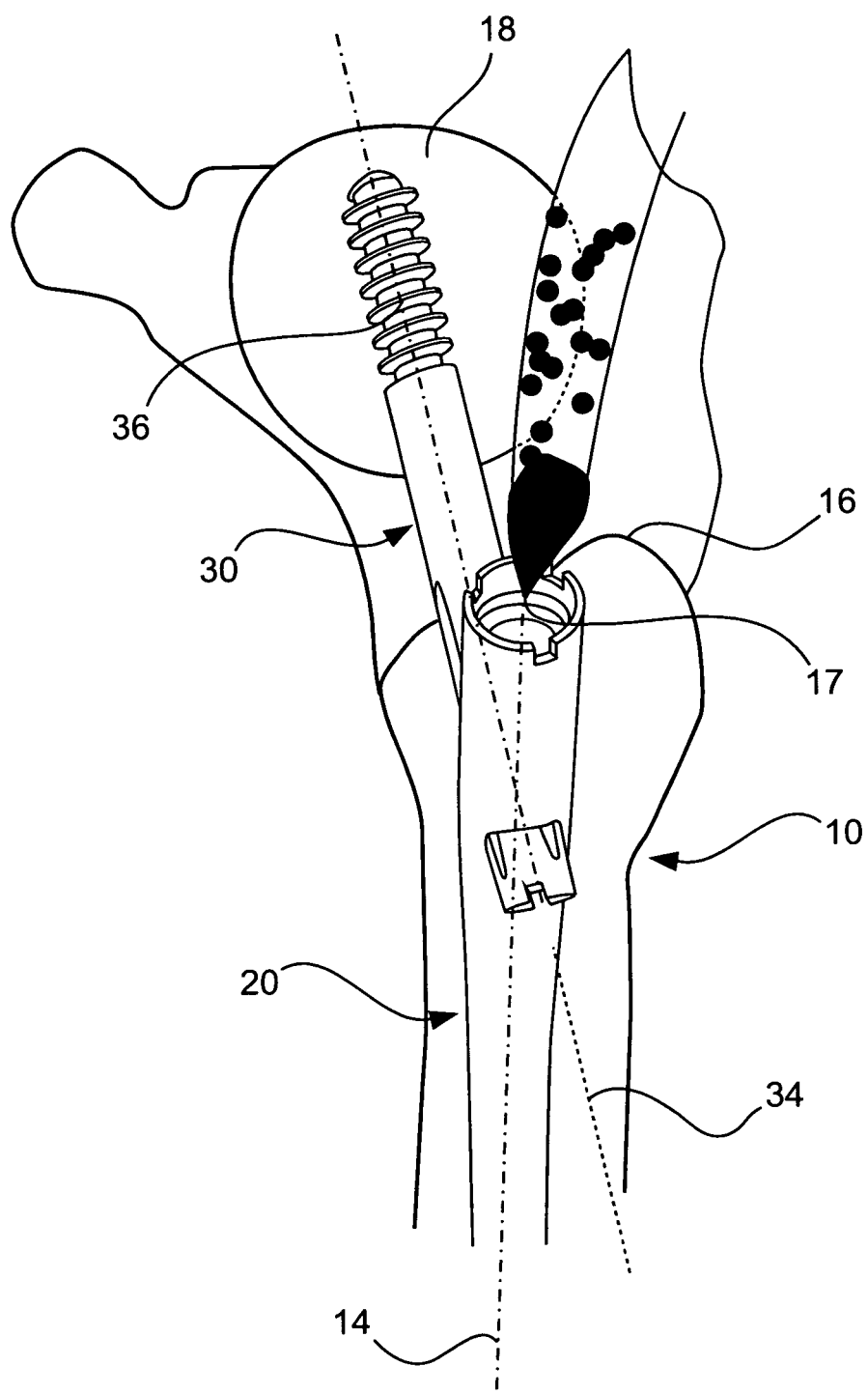
FIG. 8 shows an exemplary isometrical image including anatomical structures, a pointing device and a virtual visualization of an implant and a sub-implant.

In FIG. 8, an implant 20 together with a sub-implant 30 is shown, wherein the virtual implantation is based on a new location 17 instead of the previous location 16 from FIG. 7. The better positioned sub-implant 30 is visualized in FIG. 8 as a locking screw having a screw thread 36 extending into the head 18 of the femur 10.

While methods and devices has been illustrated and described in detail in the drawings and afore-going description, such illustrations and descriptions are to be considered illustrative or exemplary and not restrictive, the invention is not limited to the disclosed embodiments.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims.

The mere fact that certain measures are recited and mutually different dependent claims does not indicate that a combination of these measures can not be used to advantage. The computer program may be stored/distributed on a suitable medium such as an optical storage medium or a solid-state medium supplied together with or as a part of another hardware, but may also be distributed in other forms, such as via the Internet or other wired or wireless telecommunication systems. Any reference signs in the claims should not be construed as limiting the scope.

LIST OF REFERENCE SIGNS 10 femur
12 bone surface
14 shaft axis
16 location/entry point
18 head of femur
20 implant
30 sub-implant
34 axis of sub-implant
36 center point of head of femur
40 pointing device
42 tip of pointing device
44 shaft of pointing device
46 element
100 processing means
200 imaging device
220 C-arm
240 X-ray source
260 X-ray detector
300 input device
400 monitor
500 region of interest
600 database

The invention claimed is:

1. A method for assisting an insertion of an implant, the method comprising the steps of:
   determining a location on a bone surface in a first image generated from a first direction by means of an imaging unit;
   performing a first simulation of an insertion of an intramedullary rod based on the determined location, the first simulation comprising:
   identifying an implantation axis of the bone in the first image,
   aligning a virtual visualization of the intramedullary rod with the implantation axis, with respect to the determined location;
   comparing the positioning of the virtual visualization of the intramedullary rod according to the simulated insertion with an optimal virtual visualization of the intramedullary rod overlaid on the first image on an intended positioning;
   determining a deviation between the positioning of the virtual visualization of the simulated insertion and the positioning of the optimal virtual visualization of the intramedullary rod;
   resecting the bone after making a determination that the deviation falls within a predetermined range; and
   inserting the intramedullary rod into the resected bone at the determined location.

2. The method of claim 1, further comprising the steps of:
   identifying the location, determined in the first image, in a second image generated based on a bone model showing the bone from a second direction, and
   performing a second simulation of an insertion of the intramedullary rod based on the identified location, the second simulation comprising:
   identifying the implantation axis of the bone in the second image, and
   aligning a virtual visualization of the intramedullary rod with the implantation axis, with respect to the identified location.

3. The method of claim 1, further comprising the steps of:
   identifying the location, determined in the first image, in a second image generated from a second direction by means of the imaging unit, and
   performing a second simulation of an insertion of the intramedullary rod based on the identified location, the second simulation comprising:
   identifying the implantation axis of the bone in the second image, and
   aligning a virtual visualization of the intramedullary rod with the implantation axis, with respect to the identified location.

4. The method of claim 1, wherein the first simulation further comprises the step of:
   introducing a virtual visualization of a locking screw which may be implanted in combination with the intramedullary rod, and with respect to a positioning of the intramedullary rod.

5. The method of claim 1, further comprising the step of:
   if the deviation is within a predetermined range, identifying the determined location as entry point for an insertion.

6. The method of claim 1, wherein the location is automatically determined.

7. The method of claim 3, wherein the second direction is perpendicular to the first direction.

8. The method of claim 5, wherein the intended positioning includes a depth and a rotation of the intramedullary rod relative to the bone.

9. The method of claim 5, wherein the intended positioning includes a length of a locking screw.

10. The method of claim 1, wherein the first image is an X-ray image.

11. A method for assisting an insertion of an implant, the method comprising:
    obtaining a first image of the bone generated from a first direction by means of an imaging unit;
    determining a location on a bone surface in the first image;
    performing a first simulation of an insertion of an intramedullary rod based on the determined location, the first simulation comprising:
    identifying an implantation axis of the bone in the first image, using a virtual visualization of the intramedullary rod at the determined location;
    obtaining a second image of the bone generated from a second direction by means of the imaging unit;
    identifying the location, determined in the first image, in the second image based on a bone model showing the bone from the second direction;
    performing a second simulation of an insertion of the intramedullary rod based on the identified location, the second simulation comprising:
    identifying the implantation axis of the bone in the second image,
    aligning a virtual visualization of the intramedullary rod with the implantation axis of the second image, with respect to the identified location;
    comparing the positioning of the virtual visualization of the intramedullary rod according to the simulated insertion with an optimal virtual visualization of the intramedullary rod overlaid on the first and second images on an intended positioning;
    determining a deviation between the positioning of the virtual visualization of the simulated insertion with the positioning of the optimal virtual visualization of the intramedullary rod;
    resecting the bone after making a determination that the deviation falls within a predetermined range; and
    inserting the intramedullary rod into the resected bone at the determined location.

12. The method of claim 11, wherein at least one of the first and second simulations further comprises:
    introducing a virtual visualization of a locking screw which may be implanted in combination with the intramedullary rod and with respect to a positioning of the intramedullary rod.

13. The method of claim 12, further comprising:
    if the deviation is within a predetermined range, identifying the determined location as entry point for an insertion.

14. The method of claim 11, wherein the second direction is perpendicular to the first direction.

15. The method of claim 3, wherein at least one of the first and second simulations further comprises the step of:
    introducing a virtual visualization of a locking screw which may be implanted in combination with the intramedullary rod and with respect to a positioning of the intramedullary rod.

16. The method of claim 3, further comprising the steps of:
    wherein the step of determining the deviation includes determining the deviation of the positioning of the intramedullary rod and/or of a locking screw according to a simulated insertion based on the first simulation or based on the first and second simulations from an intended positioning, and if the deviation is within a predetermined range, identifying the determined location as entry point for an insertion.

17. A device for assisting an insertion of an implant, the device comprising:
   a monitor for visualizing an image of a bone;
   a pointing device including a tip and a shaft for determining a location on a bone surface in the image, which location is a possible entry point, the tip being radiopaque; and
   a processing unit adapted for performing a simulation of an insertion of an intramedullary rod into the bone with respect to the determined location, the simulation including identifying an implantation axis of the bone in the image, aligning a virtual visualization of the implant with the implantation axis, with respect to the determined location, comparing the positioning of the virtual visualization of the intramedullary rod according to the simulated insertion with an optimal virtual visualization of the intramedullary rod overlaid on the first image on an intended positioning, and determining a deviation between the positioning of the virtual visualization of the simulated insertion and the positioning of the optimal virtual visualization of the intramedullary rod, wherein a visualization of the intramedullary rod is shown in relation to the bone in the image.

18. The device of claim 17, further comprising a database for storing at least one visualization of the intramedullary rod.

19. The device of claim 18, further comprising an imaging unit for generating images of the bone from different directions.

20. The device of claim 19, wherein the image is an X-ray image.

21. The method of claim 1, wherein before the step of inserting, the method further comprises the steps of:
   determining a second location different from the previously determined location on the bone surface in the first image;
   performing a second simulation of an insertion of the implant based on the determined second location, the second simulation comprising:
   identifying a second implantation axis of the bone in the first image,
   aligning a second virtual visualization of the implant with the second implantation axis, with respect to the determined second location;
   comparing a the positioning of the second virtual visualization of the implant and/or of a sub-implant according to the second simulated insertion with the optimal virtual visualization of the implant overlaid on the first image on an intended positioning.

22. The method of claim 11, wherein the virtual visualization of the sub-implant according to the simulated insertion protrudes outside of a boundary of the bone surface in at least one of the first and second images.

* * * * *